United States Patent [19]

Lundell et al.

[11] 4,401,536

[45] Aug. 30, 1983

[54] BIOCOMPATIBLE, STEAM-STERILIZABLE IRRADIATED ARTICLES COMPRISED OF ETHYLENE COPOLYMER AND POLYPROPYLENE BLENDS

[75] Inventors: Edwin O. Lundell, North Plainfield; George T. Kwiatkowski, Green Brook, both of N.J.

[73] Assignee: Delmed, Inc., Canton, Mass.

[21] Appl. No.: 227,752

[22] Filed: Jan. 23, 1981

Related U.S. Application Data

[63] Continuation of Ser. No. 65,411, Aug. 10, 1979.

[51] Int. Cl.$^3$ ............................ C08L 23/26; A61J 1/00
[52] U.S. Cl. ................................ 204/159.2; 525/222; 525/227; 428/35
[58] Field of Search .................... 204/159.2; 428/35; 525/222, 227

[56] References Cited

U.S. PATENT DOCUMENTS

| | | | |
|---|---|---|---|
| 2,953,541 | 9/1960 | Pecha et al. | 525/227 |
| 3,389,016 | 6/1968 | Holtz et al. | 428/261 |
| 3,410,928 | 11/1968 | Baum | 525/210 |
| 3,422,055 | 1/1969 | Maloney | 260/42.46 |
| 3,426,107 | 2/1969 | Scruggs | 525/57 |
| 3,433,573 | 3/1968 | Holladay et al. | 8/169 |
| 3,537,967 | 11/1970 | Kelley et al. | 204/159.2 |
| 3,663,663 | 5/1972 | McAda | 260/42.45 |
| 3,806,558 | 4/1974 | Fischer | 525/198 |
| 3,808,047 | 4/1974 | McAda | 428/379 |
| 3,862,106 | 1/1975 | Fischer | 526/348 |
| 3,985,702 | 10/1976 | Himes | 260/33.6 AQ |
| 4,112,989 | 9/1978 | Grode et al. | 428/35 |

OTHER PUBLICATIONS

Industrial & Engineering Chemistry, "Polypropertied Polymers", vol. 45, Sep. 1953, pp. 11A & 13A.

*Primary Examiner*—Wilbert J. Briggs, Sr.
*Attorney, Agent, or Firm*—Kane, Dalsimer, Kane, Sullivan & Kurucz

[57] ABSTRACT

A semi-rigid sterilizable biomedical article for use in handling vital fluids comprising a blend of about 20–50% medical grade radiation-stabilized polypropylene by weight, the balance being a copolymer of ethylene and a comonomer selected from the group consisting of (i) vinyl esters of saturated carboxylic acids having up to 8 carbon atoms in the acid moiety, and (ii) alkyl esters of $\alpha,\beta$ ethylenically unsaturated carboxylic acids having from 3 to 8 carbon atoms in the acid moiety and from 2 to 8 carbon atoms in the alkyl moiety said comonomer comprising about 1–15 mole percent of the copolymer, said article having been irradiated to a dose of ionizing radiation ranging from about 1 to 35 Mrad.

6 Claims, No Drawings

BIOCOMPATIBLE, STEAM-STERILIZABLE IRRADIATED ARTICLES COMPRISED OF ETHYLENE COPOLYMER AND POLYPROPYLENE BLENDS

This is a continuation of application Ser. No. 65,411, filed Aug. 10, 1979.

FIELD OF THE INVENTION & DESCRIPTION OF THE PRIOR ART

The invention relates to irradiated blends of ethylene copolymer and radiation stabilized polypropylene suitable for use in fabricating biomedical articles for handling vital fluids and to articles and components of articles made from such blends.

The following are definitions and/or explanations of terms used here for purposes of clarity.

The term "toxic" means having a cumulative toxicity index (CTI) of more than 100, as measured in the *Materials Science Toxicology Laboratories Acute Toxicity Screening Program*, University of Tennessee Center for the Health Sciences, Memphis, Tenn. Conversely, "non-toxic", as used herein, indicates a CTI value of less than 100.

The term "biomedical" means suitable and/or adapted for use in biological, medical and physical science. The term "vital fluids" includes but is not limited to physiological and parenteral solutions such as blood, anticoagulated blood, blood products, other body fluids, drugs, medicines, nutritive materials, and injectable grade substances such as dextrose solution, anticoagulants, or water. Therefore, "articles and containers for the handling of vital fluids" includes bags for the storage of medication, blood bags, catheters, tubes, food wraps etc.

The term "radiation" shall mean, and shall be used interchangeably with, the term "ionizing radiation."

It is well known that ethylene copolymers retain their mechanical properties, especially their flexibility, at temperatures below −50° C. It is also well known that polypropylene retains its mechanical properties, especially its modulus, at temperatures well above 100° C. Blends of ethylene copolymers and polypropylene are also known. For example, U.S. Pat. No. 3,433,573, issued on Mar. 18, 1969 to Holladay et al. broadly discloses compositions comprising blends of a polypropylene polymer and a copolymer of ethylene. The propylene polymers envisioned contain a major amount of polypropylene and the ethylene copolymers contain a polar comonomer such as vinyl acetate, vinyl halides, vinylidene halides, vinylene carbonates, methyl methacrylate or alkyl acrylates. Within this broad compositional range blends ranging from very flexible and tough to rigid and tough may be made depending on the atactic content of the starting polypropylene and the amount of ethylene copolymer in the blend.

U.S. Pat. No. 3,433,573 further discloses that ethylene vinyl acetate/polypropylene blends have improved low temperature brittleness properties without sacrifice of the high temperature properties of polypropylene. The blends of U.S. Pat. No. 3,443,573 may be cured to induce a controlled amount of crosslinking either by incorporation in the blend of a compound which releases free radicals when heated, such as peroxide, or by subjecting the blends to irradiation with a high energy electron beam. However, these blends are not suitable for fabrication of steam sterilizable articles because unless they receive radiation doses significantly higher than those commonly used for curing, they still suffer severe distortion upon exposure to steam sterilization conditions: a temperature of about 121° C., for 30–45 minutes. Furthermore, it is well known that irradiation causes the chemical degradation of polypropylene which results in discoloration accompanied by a significant reduction in its mechanical properties. Finally, addition of peroxide as a curing agent is not permissible when the plastic is to be used for biomedical articles.

A use such as the handling of vital fluids requires the material which is to be in contact with such fluids to have inter alia the following properties:

(i) it must be substantially chemically neutral to and biologically compatible with vital fluids, it must not contain toxic amounts of potentially migratable components and it must be structurally stable;

(ii) it must be steam sterilizable i.e. it must retain its structural stability and mechanical properties and withstand steam sterilization without suffering significant distortion or significant dimensional shrinkage;

(iii) it must be heat (or radio-frequency) sealable and it must have sufficient seal strength so that it does not suffer seal failure either during steam sterilization or during the intended use of the article embodying the material; more particularly, it must be sealable to films commonly used in the manufacture of biomedical articles and components such as polyethylene, ethylene copolymers, poly(vinyl chloride) etc.;

(iv) it must possess flexibility, tensile and impact strength and other mechanical properties sufficient to protect the vital fluids during storage and other handling over the entire use temperature range of the article; for instance an article used in coupling of blood transfusion operations must have sufficient impact strength so as to be puncturable without fragmenting, and it must retain its flexibility and strength at use temperatures often as low as −80° C. or below down to temperatures of liquid nitrogen.

Polyvinyl chloride has been extensively used in the fabrication of biomedical articles. However, it requires use of a plasticizer, a component leachable into vital fluids, it is not adequately chemically neutral to such fluids, and it becomes brittle at temperatures below about −28° C., which makes it inappropriate for low temperature blood transfusion operations. Therefore, there is a need in the art for biomedical articles made from a material having all of the above properties.

In addition, it is desirable that the material remain sufficiently transparent at the desired thickness to permit convenient eye inspection and it is also desirable that it be moldable and with an outer surface receptive of inks for identification, especially when used for couplings in blood transfusion operations.

OBJECTS OF THE INVENTION

Accordingly, it is an object of this invention to provide a semi-rigid and tough plastic article suitable for use in handling vital fluids. Another object is to provide a material suitable for fabrication of a biomedical article which retains its mechanical properties over a wide use temperature range, which is heat sealable yet steam sterilizable without significant distortion or dimensional shrinkage, said material comprising a blend of ethylene copolymer and polypropylene.

Another object is to provide a formable ethylene copolymer/polypropylene blend suitable for fabrication of a steam sterilizable biomedical article comprising a blend of ethylene copolymer and polypropylene. Still another object is to provide ethylene copolymer-polypropylene blends which can easily deform to make a tight aseptic seal and which have sufficient impact resistance as to be readily puncturable without fragmenting when used for couplings in blood transfusion operations.

It is an object of this invention to employ radiation to crosslink the polymer blends to a degree sufficient to reduce distortion, yet preserve formability of the blends, heat seal strength and cohesive seal failure of articles made from such irradiated blends. Another object is to provide fabricated biomedical articles or components which can be heat sealed to polyethylene, ethylene copolymer, or vinyl polymer film.

A further object of this invention is to provide biomedical articles comprising ethylene copolymer/polypropylene blends which do not require the use of a mold-release agent when produced by conventional injection molding procedures and which do not contain toxic amounts of migratable components.

These and other objects and advantages of the invention will be apparent to those skilled in the art from the following description.

SUMMARY OF THE INVENTION

A semi-rigid sterilizable biomedical article for use in handling vital fluids comprising a blend of about 20–50% medical grade radiation-stabilized polypropylene by weight, the balance being a copolymer of ethylene and a comonomer selected from the group consisting of (i) vinyl esters of saturated carboxylic acids having up to 8 carbon atoms in the acid moiety, and (ii) alkyl esters of $\alpha,\beta$ ethylenically unsaturated carboxylic acids having from 3 to 8 carbon atoms in the acid moiety and from 2 to 8 carbon atoms in the alkyl moiety said comonomer comprising about 1–15 mole percent of the copolymer, said article having been irradiated to a dose of ionizing radiation ranging from about 1 to 35 Mrad.

A blend comprising from about 20 to 50 percent radiation stabilized polypropylene, the balance being a copolymer of ethylene and a comonomer selected from the group consisting of (i) vinyl esters of saturated carboxylic acids having up to 8 carbon atoms in the acid moiety, and (ii) alkyl esters of $\alpha,\beta$ ethylenically unsaturated carboxylic acids having from 3 to 8 carbon atoms in the acid moiety, and from 2 to 8 carbon atoms in the alkyl moiety, said comonomer comprising from about 1 to 15 mole percent of the copolymer, said blend being capable of receiving a dose of ionizing radiation from about 1 to 35 Mrad.

DETAILED DESCRIPTION OF THE INVENTION

More specifically this invention relates to a semi-rigid, formable, translucent, steam sterilizable, heat sealable irradiated article suitable for processing, storing and/or transferring blood, blood components and products, parenteral and biological solutions, and injectable grade substances. The article comprises:
  (a) a copolymer of ethylene and a comonomer selected from the group of
    (i) vinyl esters of saturated caboxylic acids having up to 8 carbon atoms in the acid moiety, and
    (ii) alkyl esters of $\alpha,\beta$ ethylenically unsaturated carboxylic acids containing from 3 to 8 carbon atoms in the acid moiety, and from 2 to 8 carbon atoms in the alkyl moiety,
    the comonomer comprising from 1 to 15 mole percent of the copolymer; blended with
  (b) radiation stabilized medical grade polypropylene, the blend containing 20–50% polypropylene by weight.

The polymers comprising the blends of this invention are irradiated to a dose of ionizing radiation up to 35 Mrads.

The radiation dose must be sufficient to reduce dimensional shrinkage during subsequent steam sterilization preferably to 10% or less, but it must not be so high as to cause significant degradation of the polypropylene. At the same time, the polypropylene content must not be so high as to make the effect of any degradation which may occur (it is well known that polypropylene degrades spontaneously over time) manifest in inferior mechanical properties and in particular, unacceptably low heat seal strengths and/or adhesive seal failures.

Preferably, the articles of this invention should be irradiated, or receive the bulk of irradiation dose, after forming. Irradiation at doses such as described above, before forming, impedes melt processing of the blends especially in molding operations, and results in articles with poor heat sealability.

Sterilization of the articles of this invention may be conveniently accomplished by steam sterilization thereof at 121° C. for 30–45 minutes. Examples of biomedical steam-sterilizable articles which can be fabricated according to this invention are catheters, shunts, cannulae, blood collection sets, containers and coupling devices, infusion sets, extracorporeal tubing sets and the like.

The articles of this invention may also be radiation sterilized if, when sterilized, they contain no substances which would be adversely affected upon exposure to ionizing radiation (e.g. radiation of anticoagulant solutions causes formation of ethylene glycol, a toxic substance). In the case of radiation sterilization the radiation dose required is much lower than that required for crosslinking usually less than 5 Mrad, and it depends on the initial microbial count in the article.

The irradiated steam sterilizable article of this invention can be further characterized as
  (1) having good resiliency and a melt index of zero;
  (2) being heat sealable to its constituent ethylene copolymer and to other polymeric film materials commonly used for biomedical articles with only cohesive failure of the seal;
  (3) having an elongation at break greater than 100%;
  (4) having a modulus of elasticity between 15,000 and 100,000 psi and preferably between 15,000 and 50,000 psi, at room temperature;
  (5) having no toxic amounts of migratable components and being biocompatible with blood components and living tissue;
  (6) having good aging characteristics and a shelf life of about 5 years.

Another embodiment of this invention involves novel compositions comprising irradiated blends of an ethylene copolymer with a radiation stabilized medical grade polypropylene suitable for use in biomedical applications. Such compositions must be structurally stable and not suffer substantial degradation upon irradiation. Therefore, the polypropylene must contain a biocompatible, Food and Drug Administration approved, stabilizer to improve its irradiability and its aging characteristics, and the polypropylene content of the blend must not exceed 50% by weight. An example of a suitable commercial product for this purpose is ARCO-J-008* radiation stabilized medical grade polypropylene.

*(a trademark of Atlantic Richfield Company, Inc.)

The blend must be able to withstand steam sterilization temperatures. Therefore, its polypropylene content must be no less than 20% by weight. A particularly preferred polypropylene content for this invention is 25% by weight. A polypropylene content greater than 50% results in an irradiated blend with reduced low temperature characteristics, and impaired seal strength and clarity. The radiation dose must be sufficient to render the blend melt index zero and to significantly reduce shrinkage upon exposure to temperatures as high as 125° C. The blends of this invention show no further improvement in properties with additional irradiation once they have received a dose of about 35 Mrad. By contrast, heat seal strength continues to decrease with increasing radiation dose.

Suitable ethylene copolymer resins include copolymers of ethylene and a comonomer selected from the group consisting of vinyl esters of saturated carboxylic acids having from 2 to 8 carbon atoms in the acid moiety and alkyl esters of $\alpha,\beta$ ethylenically unsaturated carboxylic acids, having from 3 to 8 carbon atoms in either the acid moiety and up to 8 carbon atoms in the alkyl moiety.

Examples of suitable ester monomers include methyl acrylate, ethyl acrylate, butyl acrylate, isobutyl acrylate, methyl methacrylate, ethyl maleate, methyl fumarate, vinyl acetate, vinyl propionate and the like. Preferably, the copolymer contains one of the following ester monomers: ethyl acrylate and vinyl acetate. An especially preferred copolymer is ethylene/ethyl acrylate copolymer.

Preferred ester monomer contents are 1 to 15 mole percent of the copolymer, but copolymers with an ester content up to about 50 mole percent can be used, if the requirements for end product properties are somewhat relaxed. The upper limit of 15 mole percent corresponds to that comonomer content at which the lipid solubility of the ester becomes sufficiently high as to increase the risk of potential extractables in biological fluids to an undesirable degree. The lower limit of 1 mole percent is a function of achievable heat seal strength, i.e. it is the lowest comonomer content with which an acceptable heat seal to a film comprising the same ethylene copolymer films can be practically achieved. For articles comprising ethylene copolymer films and for the ester content dependent properties of such films suitable for handling vital fluids in the form of blood packages and containers, see copending U.S. patent application Ser. No. 36,694 filed on May 7, 1979 entitled "Flexible, Sterilizable, Irradiated Plastic Articles for Handling Vital Fluids". Some comonomer content is desirable also because it increases the efficiency of the radiation cross-linking process.

For the preferred polypropylene and ester comonomer contents of the blend, the preferred radiation dose range is about 10-20 Mrad. In this range shrinkage can be limited to below 15 and even below 10%, the mechanical properties reach optimum values, especially at high temperatures, while strong heat seals are still practically feasible.

Suitable starting materials for the blend are:

(a) low-pressure, high-isotacticity polypropylene having an atactic content of less than about 10% (such polypropylene must be medical grade and possess radiation stability); approval of a particular polypropylene resin for blends of this invention depends on its exhibiting good long term storage stability, low ash- and trace metal content and resistance to radiation; and (b) an ethylene/ethyl acrylate resin containing preferably about 15% ethyl acrylate by weight, and having as many of the following properties as possible: low hexane extractables (down to 3% or less), low percentage of low molecular weight polymer chains, low volatile components, good clarity and heat sealability, and low ash metal content; an example of a suitable commercially available material is Union Carbide DPDA-6182 ethylene/ethyl acrylate copolymer resin.

Suitable blending procedures include all blending procedures involving use of shear force (Banburry-type mixers, extruders, roll mills etc). Blending procedures involving use of additives should be avoided as one of the most important aspects of the irradiated biomedical article of this invention is that it comprises a material which can be additive-free, i.e. which need contain no toxic amounts or species of plasticizers, antioxidants, lubricants, stabilizers filters or mold-release agents which might extract into the vital fluids to be handled by the article.

Thus, it is possible to fabricate an article of this invention by mixing suitable amounts of an ethylene copolymer and polypropylene by shear force to create a blend, by molding the blend into an article, or component thereof, without use of a mold-release agent and, if desired, by heat sealing said article or component onto another article, e.g. a film, the latter article preferably comprising the source ethylene copolymer. An alternative forming step may involve extrusion or another such forming technique.

After forming, the article is irradiated to the desired dose level and then steam-sterilized.

The invention is further illustrated by the following examples:

EXAMPLE 1

Blends of ethylene/ethyl acrylate (EEA) containing 12-18% ethyl acrylate (EA) by weight* and radiation stabilized medical grade polypropylene (PP) were prepared by mixing, extrusion into ⅛" strand and chopping of the strand into ⅛"×1/1" pieces, and repeated extrusion and chopping to insure uniform blending. The blends were then injection molded into small pieces (transfusion ports for use on a blood storage bag, approximate dimensions 3×½×¼ inches) without incorporation of a mold release agent. The pieces were irradiated to a dose of 20 Mrad, using a Van de Graaff electron generator and subsequently they were steam sterilized in a steam autoclave. The results are summarized in Table I, below. Mechanical properties are depicted in Table II and the relationship between steam sterilization, distortion and dose of radiation is shown in Table III. Except for transfusion ports for use in biomedical fluid containers such as blood transfusion bags, the molded articles included an injection needle housing and a one use valve, also to be used in connection with a blood transfusion bag.

*corresponding to 3.5-6.5 mole percent ethyl acrylate

TABLE I

| Sample # 10465-38 | % EEA by weight | % PP by weight | % EA IN EEA by weight | Mrad | Distortion during Steam Sterilization | *Flexibility |
|---|---|---|---|---|---|---|
| 1 | 25 | 75 | 18 | 20 | None | Stiff |
| 1A | 25 | 75 | 18 | 0 | None | Stiff |
| 2 | 50 | 50 | 18 | 20 | None | Stiff |
| 2A | 50 | 50 | 18 | 0 | None | Stiff |
| 3 | 75 | 25 | 18 | 20 | Very Small | Mod. Flex. |
| 3A | 75 | 25 | 18 | 0 | Very Small | Mod. Flex. |
| 4 | 90 | 10 | 18 | 20 | Moderate | Very Flex. |
| 4A | 90 | 10 | 18 | 0 | Severe | Very Flex. |
| 5 | 95 | 5 | 18 | 20 | Severe | Very Flex. |
| 5A | 95 | 5 | 18 | 0 | Severe | Very Flex. |
| 6 | 50 | 50 | 12 | 20 | None | Stiff |
| 6A | 50 | 50 | 12 | 0 | None | Stiff |
| 7 | 75 | 25 | 12 | 20 | None | Mod. Flex. |
| 7A | 75 | 25 | 12 | 0 | None | Mod. Flex. |
| 8 | 87.5 | 12.5 | 12 | 20 | Moderate | Mod. Flex. |
| 8A | 87.5 | 12.5 | 12 | 0 | Severe | Mod. Flex. |

TABLE II

|  | #10465-41-1 15% PP 85% (EEA 18% EA) | #10465-41-2 20% PP 80% (EEA 18% EA) | #10465-41-3 15% PP 85% (EEA 12% EA) | #10465-41-4 20% PP 80% (EEA 12% EA) |
|---|---|---|---|---|
| Tensile Modulus (psi) | 5960 | 9170 | 15,800 | 16,500 |
| Tensile Modulus (psi) | 810 | 1120 | 1320 | 1110 |
| Elongation at Break (% Wt.) | 585 | 640 | 615 | 490 |
| Pend. Impact (ft. lb./in.$^3$) | 383 | 390 | 348 | 368 |

*The flexibility characterizations "stiff" "moderately flexible" etc. are of course subjective. They represent the judgement of one skilled in the art of plastic devices and they are only provided to show a variation of flexibility with polymer content and/or irradiation dose.

TABLE III

| Sample | Irradiation Dose (Mrads) | % PP | % EEA | % EA in EEA | Distortion |
|---|---|---|---|---|---|
| 10465-38-3 | 0 | 25 | 75 | 18 | Moderate |
| 10465-38-3 | 5 | 25 | 75 | 18 | Small |
| 10465-38-3 | 10 | 25 | 75 | 18 | None |
| 10465-38-3 | 15 | 25 | 75 | 18 | None |
| 10465-38-3 | 20 | 25 | 75 | 18 | None |
| 10465-38-7 | 0 | 25 | 75 | 12 | Moderate |
| 10465-38-7 | 5 | 25 | 75 | 12 | Small |
| 10465-38-7 | 10 | 25 | 75 | 12 | None |
| 10465-38-7 | 15 | 25 | 75 | 12 | None |
| 10465-38-7 | 20 | 25 | 75 | 12 | None |

EXAMPLE 2

Blends of ethylene vinyl acetate (18% vinyl acetate by weight) and radiation stabilized medical grade polypropylene were prepared in the same manner as in Example 1. The blends were injection molded without use of a mold-release agent into the port assemblies described in Example I. The molded ports were cross-linked with varying amounts of ionizing irradiation using a Van de Graaff electron generator, then steam sterilized. The amount of distortion suffered during sterilization was noted. The results are shown below:

| Sample | % PP | % EVA | Irradiation Dose (Mrad) | Distortion |
|---|---|---|---|---|
| 11035-2 | 25 | 75 | 0 | Severe |
| 11035-2 | 25 | 75 | 5 | Small |
| 11035-2 | 25 | 75 | 10 | Small |
| 11035-2 | 25 | 75 | 20 | None |

EXAMPLE 3

40 ml thick plaques of ethylene ethyl acrylate/polypropylene blend material of different proportions were heat sealed to 12 mil ethylene/ethyl acrylate film (15% ethyl acrylate by weight). Heat seal strengths were tested after sealing, after irradiation and after steam sterilization. The results are reported below.

| Sample No. | % PP/EEA by weight | Peel Strength lbs/in | Failure Type |
|---|---|---|---|
| (a) NON-STERILIZED-NON-RADIATED | | | |
| 25-1 | 25/75 | 8.75 | Cohesive |
| 25-2 | 25/75 | 9.50 | Cohesive |
| 35-1 | 35/65 | 7.20 | Cohesive |
| 35-2 | 35/65 | 8.11 | Adhesive |
| 50-1 | 50/50 | 6.95 | Adhesive |
| 50-2 | 50/50 | 7.30 | Adhesive |
| (b) NON-STERILIZED-RADIATED TO 12.5 MRAD | | | |
| 25-3 | 25/75 | 11.3 | Cohesive |
| 25-4 | 25/75 | 16.8 | Cohesive |
| 35-3 | 35/65 | 7.79 | Cohesive |
| 35-4 | 35/65 | 7.20 | Cohesive |
| 50-3 | 50/50 | 7.30 | Adhesive |
| 50-4 | 50/50 | 6.80 | Adhesive |
| (c) STEAM STERILIZED-RADIATED TO 12.5 MRAD | | | |
| 25-5 | 25/75 | 9.40 | Adhesive |
| 25-6 | 25/75 | 10.00 | Cohesive |
| 35-5 | 35/65 | 6.70 | Adhesive |
| 35-6 | 35/65 | 6.95 | Adhesive |
| 50-5 | 50/50 | 5.50 | Adhesive |
| 50-6 | 50/50 | 6.20 | Adhesive |

What is claimed is:

1. A semi-rigid biomedical article for use in handling vital fluids consisting essentially of a blend of about 20-50% medical grade radiation stabilized polypropylene by weight, the balance being a copolymer of ethylene and a comonomer selected from the group consisting of (i) vinyl esters of saturated carboxylic acids having up to 8 carbon atoms in the acid moiety, and (ii) alkyl ester of $\alpha,\beta$ ethylenically unsaturated carboxylic acids having from 3 to 8 carbon atoms in the acid moiety and from 2 to 8 carbon atoms in the alkyl moiety said comonomer comprising about 1-15 mole percent of the copolymer, said article having been irradiated to a dose of ionizing radiation ranging from about 1 to 35 Mrad; steam sterilized; and heat-sealed; said blend being free of toxic amounts of migratable components and possessive of flexibility, tensile and impact strengths suited for handling vital fluids.

2. The article of claim 1 wherein said ethylene copolymer is selected from the group consisting of ethylene/ethyl acrylate and ethylene/vinyl acetate.

3. The article of claim 2 wherein said comonomer content ranges from about 3.5 to about 6.5 mole percent of said copolymer.

4. The article of claim 3 wherein said radiation dose ranges between about 10 and 20 Mrad.

5. The article of claims 1, 2, 3 or 4 wherein said blend comprises 25% polypropylene by weight.

6. The article of claim 4 wherein the dose is about 12.5 Mrad.